United States Patent [19]

Pfirrmann

[11] 4,107,305
[45] Aug. 15, 1978

[54] TREATMENT OF ENDOTOXAEMIA

[75] Inventor: Rolf W. Pfirrmann, Lucerne, Switzerland

[73] Assignee: Ed. Geistlich Sohne A.G. fur Chemische Industrie, Lucerne, Switzerland

[21] Appl. No.: 601,716

[22] Filed: Aug. 4, 1975

[51] Int. Cl.² .............................................. A61K 31/54
[52] U.S. Cl. .................................................... 424/246
[58] Field of Search ........................................ 424/246

[56] References Cited

PUBLICATIONS

Derwent Form Doc. #24,488, Fr. 1,458,701, published 10/65.

*Primary Examiner*—Jerome D. Goldberg
*Attorney, Agent, or Firm*—Bacon & Thomas

[57] ABSTRACT

The present invention provides a method of combatting endotoxaemia whereby there is administered to a patient an effective amount of a compound of the formula:

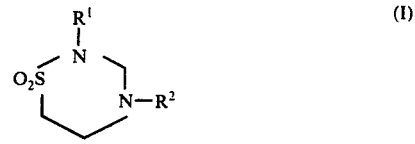

where $R^1$ is hydrogen or an alkyl group with 1–6 carbon atoms and $R^2$ is hydrogen or an alkyl group with 1–6 carbon atoms or a group of formula:

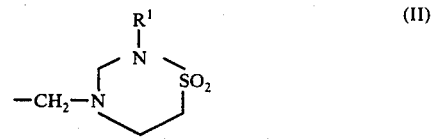

$R^1$ is preferably hydrogen and $R^2$ is preferably hydrogen or a group of formula II; the most preferred compound is bis-(1,1-dioxo-perhydro-1,2,4-thiadiazin-4-yl)-methane.

10 Claims, No Drawings

TREATMENT OF ENDOTOXAEMIA

This invention relates to improvements in or relating to the treatment of endotoxaemia.

Bacterial infections by Gram-negative organisms are commonly accompanied by endotoxaemia, that is, by the reaction of the patient to the endotoxin liberated by the organisms.

Endotoxin is a complex lipopolysaccharide constituent of the O-somatic antigen and is loosely attached to the cell walls of Gram-negative bacteria. Irrespective of the bacterial source, all endotoxins exhibit similar toxic properties - in contradistinction to the exotoxins of Gram-positive bacteria which exert a wide range of individual effects. In man it can produce the syndrome of endotoxin shock when large numbers of Gram-negative bacteria are lysed. This syndrome is encountered in about 30% of patients with Gram-negative septicaemia. The commonest predisposing factors are urinary tract infection, instrumentation of the bladder, strangulated intestinal loops, faecal peritonitis, biliary sepsis and extensive skin burns. Endotoxin appears to act on small blood vessels by means of a number of chemical mediators, e.g. the catechol amines, histamine, 5-hydroxytryptamine and bradykinin. At the subcellular level, damage to the lysosomal membranes, with release of hydrolytic enzymes, may be the primary effect.

With the increasing incidence of Gram-negative sepsis in hospitals, endotoxin shock is becoming more frequently recognized as a major complication in surgical practice, with a mortality variously reported as 30 – 70 percent. We have now found that certain perhydro-1,2,4-thiadiazine dioxides exert marked antiendotoxic action in experimental endotoxaemia. Thus, for example, pharmacological experiments in mice have shown significant protection against endotoxic shock induced by the endotoxin of E. Coli K235 135-2, while in the clinic, patients suffering from faecal peritonitis recovered particularly rapidly on treatment with the material.

According to the present invention therefore we provide a novel method of combatting endotoxaemia whereby there is administered to a patient an effective amount of a compound of the general formula

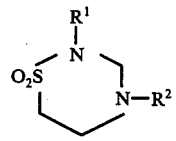

(I)

where $R^1$ is hydrogen or an alkyl group with 1–6 carbon atoms and $R^2$ is hydrogen or an alkyl group with 1–6 carbon atoms or a group of the formula

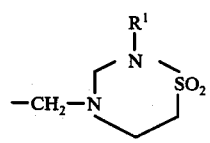

(II)

$R^1$ is preferably hydrogen and $R^2$ is preferably hydrogen or a group of formula II. The most preferred compound is bis-(1,1-dioxo-perhydro- 1,2,4-thiadiazin-4-yl)methane. Where $R^1$ or $R^2$ is alkyl, possible groups may for example be methyl, ethyl, propyl, isopropyl, butyl, pentyl or hexyl.

The above active compounds possess a low toxicity, the intraperitoneal $LD_{50}$ in mice being of the order of 1.5 g/kg.

The new method according to the invention is of particular application in the treatment of faecal peritonitis, which may, for example, occur in cases of perforated duodenal ulcer or appendix. Other endotoxic conditions include infections of the urinary tract and other body cavities such as bone cavities as in osteomyelitis and conditions induced by instrumentation of the urinary tract, strangulation of intestinal hoops, biliary sepsis and skin burns as well as the endotoxic shock accompanying the Gram-negative sepsis which is increasingly incident in hospitals.

The active compounds are thus especially useful in treatment of urinary infections and in many instances the purely bacteriostatic activity of the compounds is of great value apart from their action in combatting endotoxic effects.

In the treatment of faecal peritonitis, very considerable success has been achieved by introduction of sterile aqueous solutions of the active compound directly into the abdomen, usually before and after surgery to correct the causal condition. The drug may also be administered intravenously.

The new method is also of particular application to surgery, where opening up of large body cavities such as the abdomen always carries a risk of infection especially Gram negative sepsis and by organisms normally resident in the colon. It is especially convenient in such surgery, therefore, to irrigate the interior of the cavity, e.g. the abdomen, immediately before surgery. The antibacterial solution can be introduced by intraperitoneal injection and can eventually be removed from the peritoneum by a drainage tube. The drainage tube may conveniently be left in position after completion of surgery and one or more post-operative irrigations effected.

The active compounds are advantageously administered at a dose level of between 1 and 10 grams, depending on the type of endotoxaemia concerned and the body weight of the patient. For the treatment of faecal peritonitis, excellent results have been obtained by introduction of 1 to 6 g, for example 2 to 4 g, e.g. about 3 g, of the active compound (e.g. as a solution in 100 ml. of sterile, pyrogen-free water) directly into the abdomen. Such solutions are preferably at a concentration of between 1.0% and 2.5% of active material. In general, the concentration of active substance for combatting an established infection is preferably about 2% whereas the preferred concentration for prophylaxis is about 1%.

Although a single dose of the active substance may suffice to treat the faecal peritonitis, it may be desirable to administer a daily or twice-daily dose of the active substance (e.g. about 3 g per day) to the abdomen to prevent recurrence of the endotoxaemia and to provide an antibacterial action. This subsequent administration may be effected by an in situ catheter.

The treatment of urinary infections exhibiting endotoxic conditions is preferably by bladder irrigation, for example using an aqueous solution of the active compound.

The active compound will normally be administered in sterile, pyrogen-free water. Aqueous solutions may contain, for example, inorganic salts, for example isotonic sodium chloride. It is particularly suitable to use, instead of such salts, a solution of polyvinylpyrrolidone, e.g. at about 5% concentration.

Since Gram-negative organisms will frequently be present and since the bacteriostatic activity of the active compounds is lower than that of many conventional antibiotics, it is often advantageous to administer the substance in conjunction with a systemic antibiotic substance, more especially, a substance strongly active against Gram-negative organisms, for example ampicillin, tetracycline, cloxacillin, cephalothin, gentamycin, linocomycin, nystatin, clindamycin etc. Other substances useful for simultaneous administration with the active compound include corticosteroids, vasodilators and whole blood. For use in contact with sensitive tissues, an anaesthetic such as methocaine or lidocaine may be incorporated.

A clinical trail was effected using 9 patients selected from emergency or elective admissions who at the time of operation appeared clinically to have peritonitis, that is, they all had purulent peritoneal exudation or frank contamination by faeces.

A charcoal swab immediately inoculated into transport medium was taken from all patients prior to instillation of Taurolin (bis-1,1-dioxo-perhydro-1,2,4-thiadiazin-4-yl)-methane).

Taurolin (100mls. of 2% solution) was instilled into the abdominal cavity immediately before closure of the peritoneum or instilled after closure via the drain tube. All patients had the abdominal cavity drained by some type of tube drain for a minimum of two days post-operatively. Any supportive therapy felt to be necessary was given, no limitation being imposed because of the trial.

All patients were reviewed regularly for side effects, all necessary laboratory investigations performed.

The following results were obtained:

CASE 1: Age 28: Male; Length of stay — 26 days;
PRESENTATION: Known Ulcerative Colitis. No response to medical therapy during 4 years elective surgery.
OPERATION: Total colectomy with closure of rectal stump (Hartmann's Procedure). Large bowel extremely friable, faecal soiling of peritoneum at operation. 100mls. Taurolin instilled into abdominal cavity.
BACTERIOLOGY: *E. Coli;* Bacteroides; *Clostridium Welchii; Staph. Aureus.*
POST OPERATIVE COURSE: For 48 hours post-operatively, c/o muscle cramps, especially in the legs. Serum Calcium normal, settled spontaneously. 6th day developed pyrexia, treated with Cephaloridine and Clindamycin. 8th day discharged rectal abscess; culture — *E. Coli.* Pyrexia settled. Developed oral moniliasis which was treated with Nystatin. Discharged well on 19th post operative day; well at follow-up investigation.
CONCOMMITANT THERAPY: Multivite, Distalgesics, Concordin, Nitrazepam, Nystatin, Clindamycin, Pentazocine, Prochlorperazine, Morphine, Calcium Gluconate, Ferrous Sulphate.
CASE 2: Age 72; Female; length of stay — 30 days;
PRESENTATION: Emergency admission with large bowel obstruction and peritonitis. Known case of Ca. sigmoid colon; had previously refused operation.
OPERATION: Transverse colostomy; free fluid in abdominal cavity. Carcinoma confirmed. Tube drain fitted. 100mls. of Taurolin instilled into peritoneal cavity prior to closure.
BACTERIOLOGY: *E. Coli,* Klebsiella.
POST OPERATIVE COURSE: Became pyrexial on 3rd day; treated with Gentamycin and Lincomycin. Settled. Transfused 3 units of packed cells on 12th day for anaemia. Swollen painful calf. Discharged well on 30th day. Well at follow up.
CONCOMMITANT THERAPY: Gentamycin, Lincomycin, Dihydrocodiene, Tetracycline, Lomotil, Ferrous Sulphate, Frusemide, Ampicillin, Nystatin.
CASE 3: Age 25; Male; Length of stay — 11 days;
PRESENTATION: Perforated Duodenal Ulcer with 12 hour history. Pyrexia 37.5° C; rigid abdomen with rebound tenderness.
OPERATION: Anterior perforation with copious purulent fluid. Perforation oversewn. 100mls. of Taurolin instilled into peritoneal cavity.
BACTERIOLOGY: Monilia.
POST OPERATIVE COURSE: Mild pyrexia for 2 days post operatively. Treated with Tetracycline. Settled well. Discharged on 5th day. Well at follow up.
CONCOMMITANT THERAPY: Pethidine, Prochlorperazine, Tetracycline, Dihydrocodeine, Diazepam, Aludrox.
CASE 4: Age 29; Male; Length of stay — 5 days;
PRESENTATION: Perforated Duodenal Ulcer. 10 hour history, pyrexia of 37.8° C. Rigid abdomen with generalised rebound tenderness.
OPERATION: Anterior perforation; purulent free fluid. Perforation oversewn and patched with omentum. Tube drain fitted. 100mls. of Taurolin 2% instilled.
BACTERIOLOGY: *Staph. aureus;* Strep. Viridans.
POST OPERATIVE COURSE: Uneventful; rapid recovery; drain tube removed on second day; discharged home 4th day. Well at follow up. Small wound abscess at home; settled well.
CONCOMMITANT THERAPY: Pethidine, Prochlorperazine.
CASE 5: Age 14; Male; Length of stay — 7 days;
PRESENTATION: Sudden onset of lower abdominal pain 2 days prior to admission. Pyrexia 38.6° C. Rigid abdomen with rebound tenderness. Peritonitis; presumed perforated appendix.
OPERATION: Appendicectomy and drainage of abdomen. Tube drain fitted. 100mls. of Taurolin instilled.
BACTERIOLOGY: *E. Coli.*
POST OPERATIVE COURSE: Rapid recovery. Drain tube removed on 2nd day. Home on 6th day. Well at follow up.
CONCOMMITANT THERAPY: Gentamycin, Lincomycin, Pethidine, Dihydrocodeine, Nitrazepam.
CASE 6: Age 74; Female; Length of stay — 13 days;
PRESENTATION: Sudden onset of pain in right iliac fossa 4 days prior to admission. Pain gradually worse; became constipated; vomited 3 times; toxic; ketotic. Temp. 38.0° C. Lower abdomen rigid with rebound tenderness; maximal in right iliac fossa. Bowel sounds absent. Presumed perforated appendix with peritonitis.
OPERATION: Appendicectomy with drainage of abscess. Free pus present in abdominal cavity. Tube drain fitted. 100mls. of Taurolin instilled.
BACTERIOLOGY: Klebsiella.
POST OPERATIVE COURSE: Good recovery. Drain tube removed on 4th day. Mild wound infection from 7th to 11th day (swab grew Klebsiella). Transferred to convalescence on 7th day. Home on 13th day, well.

CONCOMMITANT THERAPY: Keflin 2G IV 6 hourly. Papaveretum, Digoxin, Triclofos.

CASE 7: Age 90; Female; Length of stay — 19 days;

PRESENTATION: Pain in right groin for 4 weeks, gradually became unwell and anorexic. 3-4 days prior to admission, painful tender swelling in right iliac fossa. Pyrexia 37.5° C. Dehydrated; toxic; tender swelling in right iliac fossa; rebound. Early peritonitis.

OPERATION: Inflamed mobile mass in caecum. Perforated with free pus in abdomen. Right hemicolectomy performed. Tube drain fitted. 100mls. Taurolin instilled.

BACTERIOLOGY: *E. Coli;* Clostridium Welchii.

POST OPERATIVE COURSE: Good recovery. Transfused 1 unit packed cells during operation. Confused 1st to 3rd days, required sedation with Heminevrin. Foul discharge from drain on 4th day. Taurolin instilled 100mls. via drain on 3rd and 4th day. Swab grew *E. Coli* and Bacteroides. Became apparent that faecal fistula had developed, instillations discontinued.

Paralytic ileus from 2nd to 6th day. Fistula closed by 7th day. Began to take diet. Thereafter good recovery. Transferred for convalescence on 19th day.

CONCOMMITANT THERAPY: Ampicillin, cloxacillin, Pethidine, Prochlorperazine, Heminevrin, Frusemide, Nitrazepam.

CASE 8: Age 77; Female; Length of stay — 15 + days

PRESENTATION: Sudden onset of abdominal pain 24 hours prior to admission. Constipated for 4 days. Pyrexial, generalised abdominal tenderness.

OPERATION: Exploratory laparotomy, perforated diverticulitis with faecal peritonitis. Loop colostomy. Tube drain to pelvis. 100mls. Taurolin instilled.

BACTERIOLOGY: *E. Coli,* Non-haemolitic Streptococci.

POST OPERATIVE COURSE: Continued pyrexia post operatively. Developed faecal fistula. Gradually settled. Faecal fistula now closed, general condition good.

CONCOMMITANT THERAPY: Gentamycin, Lincomycin. Betadene in wound.

CASE 9: Age 15; Male; Length of stay — 5 days;

PRESENTATION: Twenty-four hour history of abdominal pain settling in the right iliac fossa. Toxic, pyrexia 37.8° C. Rebound tenderness lower abdomen; most severe in right iliac fossa.

OPERATION: Perforated appendix with peritonitis. Appendix excised, peritoneal cavity sucked out. Taurolin 100mls. instilled. Tube drain fitted.

BACTERIOLOGY: *E. Coli.*

POST OPERATIVE COURSE: Rapid recovery. Drain out second day. Home fourth day.

CONCOMMITANT THERAPY: Ampicillin; Pethidine; Pentazocine; Distalgesics; Promethazine.

GENERAL OBSERVATIONS

1. In all cases (1,2,3,4,7,8) in which Taurolin was poured directly into the peritoneal cavity, no observable tissue reaction occurred. All drains were tubes which were spigotted post-operatively for 2 hours then put on free drainage (in cases 7,8, suction drains).

2. Post-operatively all drains were removed as soon as drainage was minimal. In case 7 Taurolin was easily introduced via the drain by the nursing staff. No abnormal material was seen to drain from any of the cases. In cases 7 & 8, the presence of faecal fistulae were noted at once by the nursing staff.

3. No abnormal reactions were noted in any of the patients except Case 1. He had unpleasant muscle cramps for 2 days post-operatively. These could not be accounted for. Resolved spontaneously and as they did not appear in any of the other patients, were not attributed to the Taurolin.

In particular, the Anaesthetists noted no abnormality during anaesthesia despite a wide variety of techniques and agents.

No unexplained abnormalities appeared in any of the laboratory tests performed nor did any of the wide variety of drugs used exhibit any unusual effects.

4. Although the dosages used in this preliminary trial were deliberately kept low, Taurolin had no detectable side effects and would appear to be perfectly safe when used intraperitoneally. No cross reaction with other drugs could be detected.

The following case-history illustrates use of the method in combatting osteomyelitis: The patient had been treated with antibiotics for eight years resulting in loss of one kidney and damage to the second kidney. The tibia was infected with *E. Coli* and *pseudomonas.* Taurolin (8 ml; 2% by weight) was injected into the fistula of the infected tibia near one end and this treatment was given twice a day for ten days. After 3 days, firm granular tissue had formed in the fistula and after ten days the lesion had healed.

The following Examples of compositions of use in the method according to the invention is given by way of illustration only:

EXAMPLE 1

Bis-(1,1-dioxo-perhydro-1,2,4-thiadiazin-4-yl)-methane — 400 g
Polyvinylpyrrolidone (Kollidone 17) — 1000 g
Sterile water — to 20 liters 15 liters double distilled pyrogen free water are filled into a 25 liter glass vessel with stirrer and intensive reflux device and heated to 50° C with stirring. The bactericide (400 g) is added followed by PVP (Kollidone 17; 1000 g). After dissolution, the solution is cooled and the pH adjusted to 6.0 with a few drops of 0.1 N hydrochloric acid. The solution is then passed through an adsorption filter to remove microorganisms and pyrogens and through a sterilising millipore filter before being filled into 100 ml vials which are finally autoclaved.

EXAMPLE 2

A similar formulation to that of Example 1 can be prepared using as active substance 1,1-dioxo-perhydro-1,2,4-thiadiazine.

EXAMPLE 3

A similar formulation to that of Example 1 can be prepared using as active substance bis-(2-propyl-1,1-dioxo-perhydro-1,2,4-thiadiazine-4-yl) methane.

I claim:

1. A method for treating a patient suffering from endotoxaemia wherein an effective amount to reduce or eliminate endotoxaemia of a compound of the formula:

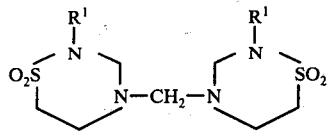

where $R^1$ is hydrogen or alkyl having 1-6 carbon atoms is administered to said patient.

2. A method as claimed in claim 1 in which said active compound is administered to a patient suffering from faecal peritonitis.

3. A method as claimed in claim 2 in which the said active compound is administered by introduction directly into the abdomen of the patient.

4. A method as claimed in claim 1 in which the said active compound is administered at a dose level between 1 and 6 g per patient.

5. A method as claimed in claim 2 in which the said active compound is administered at a dose level between 2 and 4 g per patient.

6. A method as claimed in claim 1 in which the said active compound is administered in solution or suspension in a sterile, pyrogen-free parenterally acceptable aqueous vehicle.

7. A method as claimed in claim 6 in which the concentration of said active compound in the vehicle is between 1.0% and 2.5%.

8. A method for treatment of endotoxaemia as claimed in claim 1 in which said active compound is bis-(1,1-dioxo-perhydro-1,2,4-thiadiazin-4-yl)-methane.

9. A method as claimed in claim 1 for the treatment of osteomyelitis exhibiting endotoxic conditions whereby an effective amount of said active compound is administered to a patient suffering from osteomyelitis.

10. A method as claimed in claim 1 wherein said active compound is administered by irrigation into a body cavity during surgery to cure endotoxaemia.

* * * * *